(12) United States Patent
Pfrengle et al.

(10) Patent No.: US 7,968,717 B2
(45) Date of Patent: *Jun. 28, 2011

(54) CRYSTALLINE ANHYDRATE WITH ANTICHOLINERGIC EFFICACY

(75) Inventors: Waldemar Pfrengle, Biberach (DE); Peter Sieger, Mittelbiberach (DE)

(73) Assignee: Boehringer Ingelhein International GmbH, Ingelheim (DE)

( * ) Notice: Subject to any disclaimer, the term of this patent is extended or adjusted under 35 U.S.C. 154(b) by 1601 days.

This patent is subject to a terminal disclaimer.

(21) Appl. No.: 10/976,624

(22) Filed: Oct. 29, 2004

(65) Prior Publication Data

US 2005/0143410 A1      Jun. 30, 2005

Related U.S. Application Data

(60) Provisional application No. 60/528,338, filed on Dec. 10, 2003.

(30) Foreign Application Priority Data

Nov. 3, 2003  (EP) .................................... 03025077

(51) Int. Cl.
    *C07D 491/18*      (2006.01)
(52) U.S. Cl. ......................................... 546/91; 514/291
(58) Field of Classification Search ............... 546/91; 514/291

See application file for complete search history.

(56) References Cited

U.S. PATENT DOCUMENTS

| | | | |
|---|---|---|---|
| 5,610,163 A | 3/1997 | Banholzer et al. | |
| 6,608,055 B2 * | 8/2003 | Sieger et al. | 514/229.8 |
| RE39,820 E | 9/2007 | Banholzer et al. | |
| 2004/0087793 A1 | 5/2004 | Banholzer et al. | |

FOREIGN PATENT DOCUMENTS

| | | |
|---|---|---|
| EP | 0418716 A1 | 9/1990 |
| WO | WO 02/30928 | 4/2002 |

OTHER PUBLICATIONS

Byrn, S.R. et. al. Chapter 3 "The X-Ray Powder Diffraction Method" in Solid State Chemistry of Drugs 2nd Edition, SSCI, 1999, pp. 59-67.*

Littner, M. R. et. al. "Long-Acting Bronchodilation with Once-Daily Dosing of Tiotropium (Spiriva) in Stable Chronic Obstructive Pulmonary Disease" American Journal of Respiratory and Critical Care Medicine 2000, 161, 1136-1142.*

"Guidelines for Authors" Journal of Organic Chemistry 2007, 72, 13A-27A.*

Zell et. al. "Investigation of Polymorphism in Aspartame and Neotame Using Solid-State NMR Spectroscopy." Tetrahedron 2000, 56, 6603-6616.*

Stahl, P.H., et al. "Handbook of Pharmaceutical Salts Properties, Selection and Use", 2002, Wiley-VCH, Weinheim-New York, p. 98, XP002268934.

B.Disse, et al. "Tiotopium (SpirivaTM): Mechanistical Considerations and Clinical Profile in Obstructive Lung Disease" Life Sciences, vol. 64, Nos. 6/7, p. 457-464, 1999.

Docoslis et al.; Characterization of the Distribution, Polymorphism, and Stability of Nimodipine in Its Solid Dispersions in Polyethylene Glycol by Micro-Raman Spectroscopy and Powder X-Ray Diffraction; The AAPS Journal 2007; vol. 9; No. 3; Article 43; pp. E361-E370.

Brittain; Physical Characterization of Pharmaceutical Solids; Drugs and the Pharmaceutical Sciences; vol. 70; pp. 2-35, 1995.

* cited by examiner

*Primary Examiner* — Janet L Andres
*Assistant Examiner* — D K O'Dell
(74) *Attorney, Agent, or Firm* — Michael P. Morris; Wendy A. Petka

(57) ABSTRACT

The invention relates to a new crystalline anhydrate of tiotropium bromide, processes for preparing it and its use for preparing a pharmaceutical composition for the treatment of respiratory complaints, particularly for the treatment of COPD (chronic obstructive pulmonary disease) and asthma.

10 Claims, 2 Drawing Sheets

Figure 1:
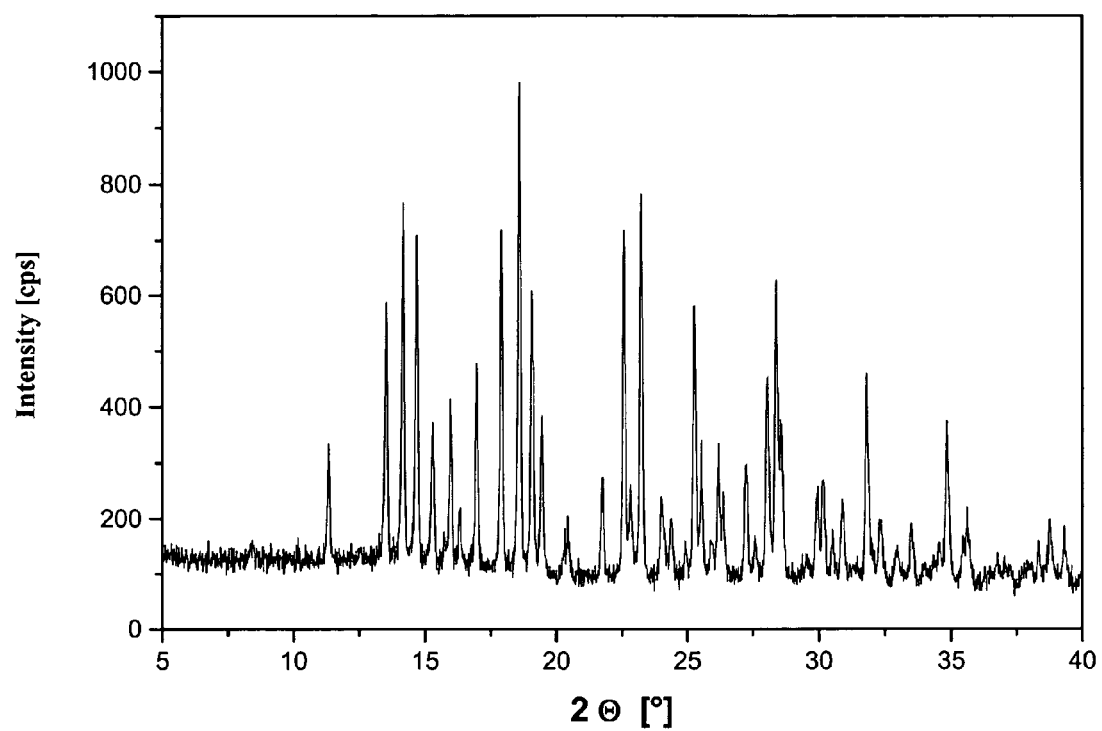

Figure 1: X-ray powder diagram of anhydrous crystalline tiotropium bromide

CRYSTALLINE ANHYDRATE WITH ANTICHOLINERGIC EFFICACY

RELATED APPLICATIONS

Benefit of U.S. Provisional Application Ser. No. 60/528,338, filed on Dec. 10, 2003, is hereby claimed, and which application is incorporated herein in its entirety.

FIELD OF THE INVENTION

The invention relates to a new crystalline anhydrate of tiotropium bromide, processes for preparing it and its use for preparing a pharmaceutical composition for the treatment of respiratory complaints, particularly for the treatment of COPD (chronic obstructive pulmonary disease) and asthma.

BACKGROUND TO THE INVENTION

Tiotropium bromide is known from European Patent Application EP 418 716 A1 and has the following chemical structure:

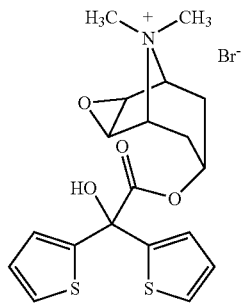

Tiotropium bromide is a highly effective anticholinergic with a long-lasting effect, which may be used to treat respiratory complaints, particularly COPD (chronic obstructive pulmonary disease) and asthma. By tiotropium is meant the free ammonium cation.

Tiotropium bromide is preferably administered by inhalation. Suitable inhalable powders packed into appropriate capsules (inhalettes) may be used. Alternatively, it may be administered by the use of suitable inhalable aerosols. These also include powdered inhalable aerosols which contain, for example, HFA134a, HFA227 or mixtures thereof as propellent gas.

The correct manufacture of the abovementioned compositions which are suitable for use for the administration of a pharmaceutically active substance by inhalation is based on various parameters which are connected with the nature of the active substance itself. In pharmaceutical compositions which are used like tiotropium bromide in the form of inhalable powders or inhalable aerosols, the crystalline active substance is used in ground (micronised) form for preparing the formulation. Since the pharmaceutical quality of a pharmaceutical formulation requires that the active substance should always have the same crystalline modification, the stability and properties of the crystalline active substance are subject to stringent requirements from this point of view as well. It is particularly desirable that the active substance should be prepared in the form of a uniform and clearly defined crystalline modification. It is also particularly desirable that the active substance be prepared in a crystalline form which is characterised by a high degree of stability even over long storage periods. The lower the tendency of a crystalline modification to absorb moisture, for example, the greater the physical stability of its crystal structure.

The aim of the invention is therefore to provide a new stable crystal form of the compound tiotropium bromide which meets the high demands mentioned above that are made of any pharmaceutically active substance. The present invention sets out in particular to provide a crystalline modification of tiotropium bromide which has only limited hygroscopic characteristics.

DETAILED DESCRIPTION OF THE INVENTION

It has been found that, depending on the choice of the conditions which may be used during the purification of the crude product obtained after industrial production, tiotropium bromide may be obtained in different crystalline modifications.

It has been found that these different modifications can be decisively obtained by the choice of solvents used for the crystallisation and by the choice of the operating conditions selected during the crystallisation process.

It has surprisingly been found that, starting from the monohydrate of tiotropium bromide, which can be obtained in crystalline form by choosing specific reaction conditions and which was described in the prior art for the first time in WO 02/30928, an anhydrous crystal modification of tiotropium bromide may be obtained which meets the high requirements set out above and thereby solves the problem underlying the present invention. Accordingly, the present invention relates to this crystalline anhydrous tiotropium bromide. Any reference made within the scope of the present invention to the term tiotropium bromide anhydrate is to be regarded as a reference to the crystalline anhydrous tiotropium bromide according to the invention.

In another aspect the present invention relates to a method of preparing the new crystalline form of anhydrous tiotropium bromide which is explained by way of example in the experimental section that follows.

The anhydrous tiotropium bromide according to the invention is particularly characterised by slightly hygroscopic characteristics, which ensure a high degree of stability of the crystal modification. The crystalline tiotropium bromide anhydrate according to the invention is highly crystalline and is therefore particularly well suited to the preparation of pharmaceutical formulations for administration by inhalation.

The present invention also relates to the use of the crystalline tiotropium bromide anhydrate according to the invention for preparing a pharmaceutical composition for the treatment of respiratory complaints, particularly for the treatment of COPD and/or asthma.

The Examples that follow serve to illustrate the present invention still further, without restricting the scope of the invention to the embodiments by way of example that follow.

A. I. Starting Materials

Tiotropium Bromide Monohydrate:

Tiotropium bromide, which was obtained for example using the method described in European Patent Application EP 418 716, was converted into crystalline tiotropium bromide monohydrate according to the disclosure of WO 02/30928. This is used as the starting compound for preparing the tiotropium bromide anhydrate according to the invention.

A. II. Examples OF Synthesis According tO tThe Invention

Example 1

10.0 g of tiotropium bromide monohydrate were taken up in 100 ml of water and dissolved at boiling temperature. Then 80.0 g of ammonium fluoride were added. After 18 hours' stirring at about 20-25° C. the product that crystallises out is isolated and dried at 70° C. The crude product obtained is dissolved in 25 ml of methanol at boiling temperature, filtered hot and cooled to ambient temperature (approx. 20-25° C.). The product that crystallises out immediately after the wall of the flask has been scratched (with a glass rod) is isolated and dried at 50° C.

Yield: 7.35 g tiotropium bromide anhydrate, white solid.

Example 2

4.39 g tiotropium bromide monohydrate were taken up in 25 ml of methanol and dissolved at boiling temperature. The clear solution is inoculated with a few crystals of the crystalline tiotropium bromide anhydrate obtained according to Example 1. The product crystallises out in the warm. After slowly cooling to ambient temperature (approx. 20-25° C.) the precipitate obtained is filtered off and dried at 50° C. Yield: 3,47 g tiotropium bromide anhydrate, white solid.
A. III. Characterisation of the Tiotropium Bromide Anhydrate According TO The Invention The tiotropium bromide anhydrate obtained by the above method is highly crystalline. It was investigated further by X-ray powder diffraction. The following procedure was used to record the X-ray powder diagram detailed below.

The X-ray powder diagram was recorded within the scope of the present invention using a Bruker D8 Advanced with a location-sensitive detector ($CuK_\alpha$-radiation, $\lambda$=1.5418 Å, 30 kV, 40 mA).

The X-ray powder diagram obtained for the tiotropium bromide anhydrate according to the invention is shown in FIG. 1.

The following Table 1 lists the characteristic peaks and standardised intensities.

TABLE 1

| 2 Θ [°] | $d_{hkl}$[Å] | intensity [%] |
|---|---|---|
| 8.39 | 10.53 | 4 |
| 11.33 | 7.80 | 27 |
| 13.50 | 6.55 | 53 |
| 14.13 | 6.26 | 65 |
| 14.70 | 6.02 | 73 |
| 15.28 | 5.79 | 31 |
| 15.72 | 5.63 | 7 |
| 15.98 | 5.54 | 33 |
| 16.32 | 5.43 | 11 |
| 16.95 | 5.23 | 45 |
| 17.90 | 4.95 | 76 |
| 18.55 | 4.78 | 100 |
| 19.07 | 4.65 | 62 |
| 19.46 | 4.56 | 36 |
| 20.32 | 4.37 | 10 |
| 20.40 | 4.35 | 12 |
| 21.75 | 4.08 | 23 |
| 22.60 | 3.93 | 77 |
| 22.83 | 3.89 | 20 |
| 23.21 | 3.83 | 86 |
| 24.01 | 3.70 | 17 |
| 24.40 | 3.64 | 13 |
| 24.93 | 3.57 | 8 |
| 25.27 | 3.52 | 60 |
| 25.55 | 3.48 | 28 |
| 25.95 | 3.43 | 7 |
| 26.21 | 3.40 | 30 |
| 26.38 | 3.38 | 18 |
| 27.26 | 3.27 | 24 |
| 27.60 | 3.23 | 8 |
| 28.07 | 3.18 | 44 |
| 28.38 | 3.14 | 67 |
| 28.58 | 3.12 | 35 |

TABLE 1-continued

| 2 Θ [°] | $d_{hkl}$[Å] | intensity [%] |
|---|---|---|
| 29.93 | 2.98 | 19 |
| 30.18 | 2.96 | 21 |
| 30.52 | 2.93 | 10 |
| 30.91 | 2.89 | 17 |
| 31.82 | 2.81 | 46 |
| 32.32 | 2.77 | 13 |
| 32.94 | 2.72 | 7 |
| 33.49 | 2.67 | 13 |
| 34.80 | 2.58 | 31 |

In the above Table the value "2 Θ [°]" represents the diffraction angle in degrees and the value "$d_{hkl}$ [Å]" represents the specified lattice plane intervals in Å.
The present invention therefore relates to crystalline tiotropium bromide anhydrate which is characterised in that in the X-ray powder diagram it has the characteristic values d = 6.02 Å; 4.95 Å; 4.78 Å; ; 3.93 Å and 3.83 Å, inter alia.

B. Formulations Containing the Tiotropium Bromide Anhydrate According to the Invention The crystalline tiotropium bromide anhydrate according to the invention is highly crystalline and is therefore particularly well suited to the preparation of, for example, pharmaceutical formulations for administration by inhalation such as inhalable powders or for example propellant-containing aerosol formulations, particularly inhalable powders and propellant-containing aerosol suspensions.
B.1. Inhalable Powders The present invention also relates to inhalable powder containing 0.001 to 3% tiotropium in the form of the crystalline tiotropium bromide anhydrate according to the invention combined with a physiologically acceptable excipient. By tiotropium is meant the ammonium cation.

Inhalable powders which contain 0.01 to 2% tiotropium are preferred according to the invention. Particularly preferred inhalable powders contain tiotropium in an amount from about 0.03 to 1%, preferably 0.05 to 0.6%, particularly preferably 0.06 to 0.3%. Of particular importance according to the invention, finally, are inhalable powders which contain about 0.08 to 0.22% tiotropium.

The amounts of tiotropium specified above are based on the amount of tiotropium cation contained.

The excipients that are used for the purposes of the present invention are prepared by suitable grinding and/or screening using current methods known in the art. The excipients used according to the invention may also be mixtures of excipients which are obtained by mixing excipient fractions of different mean particle sizes.

Examples of physiologically acceptable excipients which may be used to prepare the inhalable powders for use in the inhalettes according to the invention include monosaccharides (e.g. glucose, fructose or arabinose), disaccharides (e.g. lactose, saccharose, maltose, trehalose), oligo- and polysaccharides (e.g. dextrans, dextrins, maltodextrin, starch, cellulose), polyalcohols (e.g. sorbitol, mannitol, xylitol), cyclodextrins (e.g. α-cyclodextrin, β-cyclodextrin, χ-cyclodextrin, methyl-β-cyclodextrin, hydroxypropyl-β-cyclodextrin), amino acids (e.g. arginine hydrochloride) or salts (e.g. sodium chloride, calcium carbonate), or mixtures thereof. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. The average particle size may be determined using methods known in the art (cf. for example WO 02/30389, paragraphs A and C). Finally, in order to prepare the inhalable powders according to the invention, micronised crystalline tiotropium bromide anhydrate, which is preferably characterised by an average particle size of 0.5 to 10 μm, particularly preferably from 1 to 5 μm, is added to the excipient mixture (cf. for example WO 02/30389, paragraph B). Processes for grinding and micronising active substances are known from the prior art.

If no specifically prepared excipient mixture is used as the excipient, it is particularly preferable to use excipients which have a mean particle size of 10-50 μm and a 10% fine content of 0.5 to 6 μm.

By average particle size is meant here the 50% value of the volume distribution measured with a laser diffractometer using the dry dispersion method. The average particle size may be determined using methods known in the art (cf. for example WO 02/30389, paragraphs A and C). Analogously, the 10% fine content in this instance refers to the 10% value of the volume distribution measured using a laser diffractometer. In other words, for the purposes of the present invention, the 10% fine content denotes the particle size below which 10% of the quantity of particles is found (based on the volume distribution).

The percentages given within the scope of the present invention are always percent by weight, unless specifically stated to the contrary.

In particularly preferred inhalable powders the excipient is characterised by a mean particle size of 12 to 35 μm, particularly preferably from 13 to 30 μm.

Also particularly preferred are those inhalable powders wherein the 10% fine content is about 1 to 4 μm, preferably about 1.5 to 3 μm.

The inhalable powders according to the invention are characterised, in accordance with the problem on which the invention is based, by a high degree of homogeneity in the sense of the accuracy of single doses. This is in the region of <8%, preferably <6%, most preferably <4%.

After the starting materials have been weighed out the inhalable powders are prepared from the excipient and the active substance using methods known in the art. Reference may be made to the disclosure of WO 02/30390, for example. The inhalable powders according to the invention may accordingly be obtained by the method described below, for example. In the preparation methods described hereinafter the components are used in the proportions by weight described in the above-mentioned compositions of the inhalable powders.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

The present invention also relates to the use of the inhalable powders according to the invention for preparing a pharmaceutical composition for the treatment of respiratory complaints, particularly for the treatment of COPD and/or asthma.

The inhalable powders according to the invention may for example be administered using inhalers which meter a single dose from a reservoir by means of a measuring chamber (e.g. according to U.S. Pat. No. 4,570,630A) or by other means (e.g. according to DE 36 25 685 A).

Preferably, however, the inhalable powders according to the invention are packed into capsules (to make so-called inhalettes), which are used in inhalers such as those described in WO 94/28958, for example.

Figure 2:
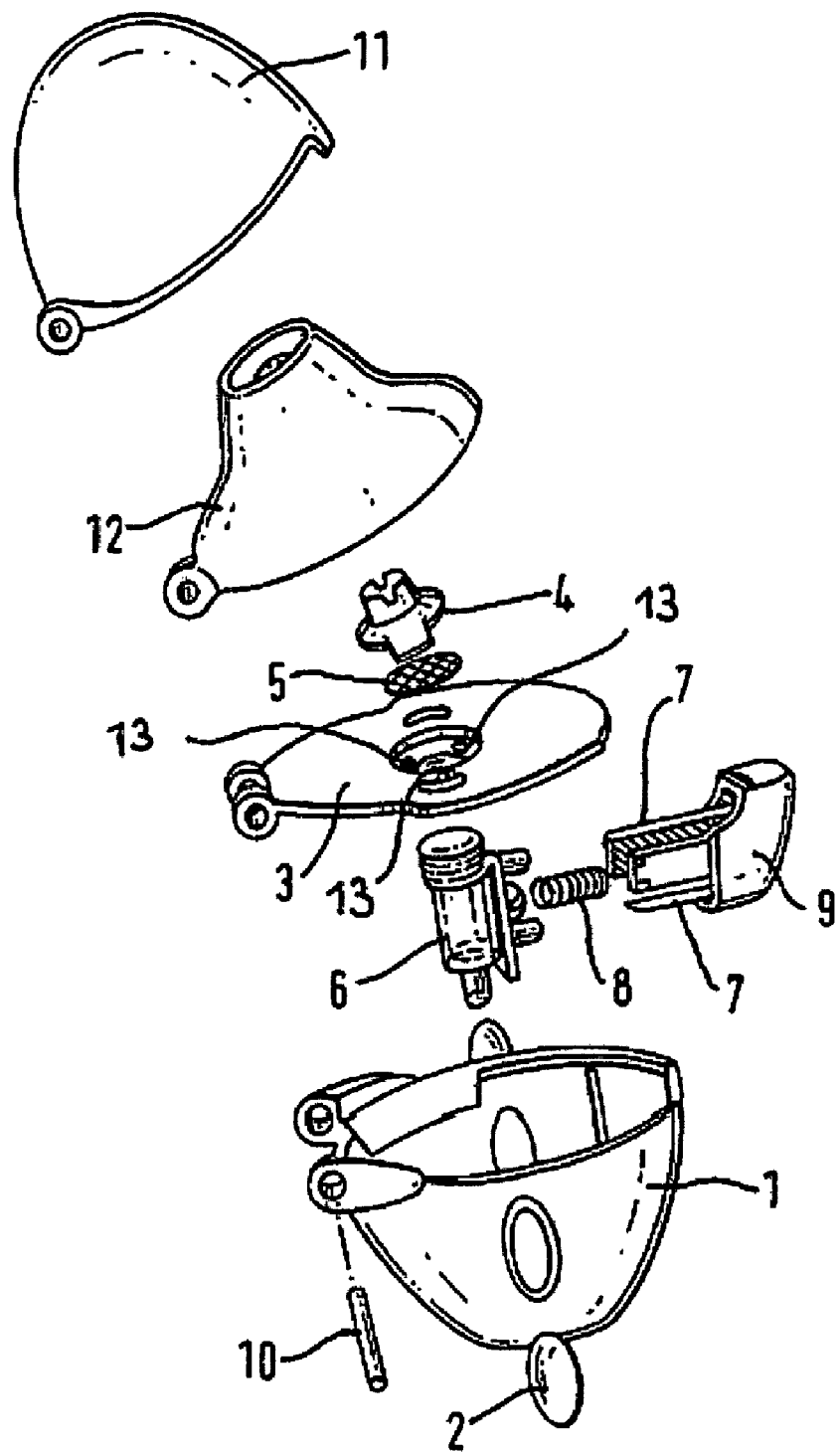

Most preferably, the capsules containing the inhalable powder according to the invention are administered using an inhaler as shown in FIG. 2. This inhaler is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and airholes 13 for adjusting the flow resistance.

The present invention further relates to the use of the inhalable powders containing the crystalline tiotropium bromide anhydrate according to the invention for preparing a pharmaceutical composition for treating respiratory complaints, particularly for the treatment of COPD and/or asthma, characterised in that the inhaler described above and shown in FIG. 2 is used.

For administering the inhalable powders containing the crystalline tiotropium bromide anhydrate according to the invention using powder-filled capsules it is particularly preferred to use capsules the material of which is selected from among the synthetic plastics, most preferably selected from among polyethylene, polycarbonate, polyester, polypropylene and polyethylene terephthalate. Particularly preferred synthetic plastic materials are polyethylene, polycarbonate or polyethylene terephthalate. If polyethylene is used as one of the capsule materials which is particularly preferred according to the invention, it is preferable to use polyethylene with a density of between 900 and 1000 kg/m$^3$, preferably 940-980 kg/m$^3$, more preferably about 960-970 kg/m$^3$ (high density polyethylene). The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the above-mentioned capsules which contain the abovementioned inhalable powder according to the invention. These capsules may contain about 1 to 20 mg, preferably about 3 to 15 mg, most preferably about 4 to 12 mg of inhalable powder. Preferred formulations according to the invention contain 4 to 6 mg of inhalable powder. Of equivalent importance according to the invention are capsules for inhalation which contain the formulations according to the invention in an amount of from 8 to 12 mg.

The present invention also relates to an inhalation kit consisting of one or more of the above capsules characterised by a content of inhalable powder according to the invention in conjunction with the inhaler according to FIG. 2.

The present invention also relates to the use of the above-mentioned capsules characterised by a content of inhalable powder according to the invention, for preparing a pharmaceutical composition for treating respiratory complaints, especially for treating COPD and/or asthma.

Filled capsules which contain the inhalable powders according to the invention are produced by methods known in the art, by filling the empty capsules with the inhalable powders according to the invention.

B.1.1. Examples of Inhalable Powders According To The Invention

The following Examples serve to illustrate the present invention in more detail without restricting the scope of the invention to the exemplifying embodiments that follow.

B.1.1.1. Starting Materials

Active Substance

The crystalline tiotropium bromide anhydrate according to the invention is used to produce the inhalable powders according to the invention. The micronisation of this active substance is carried out analogously to methods known in the art (cf for example WO 03/078429 A1). Where reference is made within the scope of the present invention to the mean particle size of the crystalline tiotropium bromide anhydrate according to the invention, this is determined using methods of measurement known in the art (cf for example WO 03/078429 A1, para. D.2).

Excipient:

In the Examples that follow lactose-monohydrate is used as excipient. It may be obtained for example from Borculo Domo Ingredients, Borculo/NL under the product name Lactochem Extra Fine Powder. The specifications according to the invention for the particle size and specific surface area are met by this grade of lactose. For example, in the Examples that follow, batches of lactose were used having the following specifications:

B.1.1.2. Preparation of the Powder Formulations According to the Invention:

I) Apparatus

The following machines and equipment, for example, may be used to prepare the inhalable powders:

Mixing container or powder mixer: Turbulamischer 2 L, Type 2C; made by Willy A. Bachofen AG, CH-4500 Basel Hand-held screen: 0.135 mm mesh size The empty inhalation capsules may be filled with inhalable powders containing tiotropium by hand or mechanically. The following equipment may be used.

Capsule Filling Machine:

MG2, Type G100, manufacturer: MG2 S.r.l, I-40065 Pian di Macina di Pianoro (BO), Italy.

Formulation Example 1

Powder Mixture:

To prepare the powder mixture, 299.39 g of excipient and 0.61 g of micronised crystalline tiotropium bromide anhydrate are used.

About 40-45 g of excipient are placed in a suitable mixing container through a hand-held screen with a mesh size of 0.315 mm. Then crystalline tiotropium bromide anhydrate in batches of about 90-110 mg and excipient in batches of about 40-45 g are screened in in alternate layers. The excipient and active substance are added in 7 and 6 layers, respectively.

Having been screened in, the ingredients are then mixed (mixing speed 900 rpm). The final mixture is passed twice more through a hand-held screen and then mixed again at 900 rpm.

Using the method described in Example 1 it is possible to obtain inhalable powders which when packed into suitable plastic capsules may be used to produce the following capsules for inhalation, for example:

Formulation Example 2

| | |
|---|---|
| tiotropium bromide anhydrate: | 0.0113 mg |
| lactose monohydrate: | 5.4887 mg |
| capsule: | 100.0 mg |
| Total: | 105.5 mg |

Formulation Example 3

| | |
|---|---|
| tiotropium bromide anhydrate: | 0.0225 mg |
| lactose monohydrate: | 5.4775 mg |
| polyethylene capsules: | 100.0 mg |
| Total: | 105.5 mg |

Formulation Example 4

| | |
|---|---|
| tiotropium bromide anhydrate: | 0.0056 mg |
| lactose monohydrate: | 5.4944 mg |
| polyethylene capsules: | 100.0 mg |
| Total: | 105.5 mg |

Formulation Example 5

| | |
|---|---|
| tiotropium bromide anhydrate: | 0.0113 mg |
| lactose monohydrate:* | 5.4887 mg |
| capsule: | 100.0 mg |
| Total: | 105.5 mg |

*the lactose contains 5% specifically added fine content of micronised lactose monohydrate with a mean particle size of about 4 μm.

Formulation Example 6

| | |
|---|---|
| tiotropium bromide anhydrate: | 0.0225 mg |
| lactose monohydrate:* | 5.4775 mg |
| polyethylene capsules: | 100.0 mg |
| Total: | 105.5 mg |

*the lactose contains 5% specifically added fine content of micronised lactose monohydrate with a mean particle size of about 4 μm.

Formulation Example 7

| | |
|---|---:|
| tiotropium bromide anhydrate: | 0.0056 mg |
| lactose monohydrate:* | 5.4944 mg |
| polyethylene capsules: | 100.0 mg |
| Total: | 105.5 mg |

*the lactose contains 5% specifically added fine content of micronised lactose monohydrate with a mean particle size of about 4 μm.

B.2. Propellant-containing Aerosol Suspensions Containing Crystalline Tiotropium Bromide Anhydrate The crystalline tiotropium bromide anhydrate according to the invention may optionally also be administered in the form of propellant-containing inhalable aerosols. Aerosol suspensions are particularly suitable for this.

The present invention therefore also relates to suspensions of the crystalline tiotropium bromide anhydrate according to the invention in the propellent gases HFA 227 and/or HFA 134a, optionally combined with one or more other propellent gases, preferably selected from the group consisting of propane, butane, pentane, dimethylether, $CHClF_2$, $CH_2F_2$, $CF_3CH_3$, isobutane, isopentane and neopentane.

According to the invention those suspensions which contain as propellent gas only HFA 227, a mixture of HFA 227 and HFA 134a or only HFA 134a are preferred.

If a mixture of the propellent gases HFA 227 and HFA134a is used in the suspension formulations according to the invention, the weight ratios in which these two propellent gas components are used are freely variable.

If one or more other propellent gases, selected from the group consisting of propane, butane, pentane, dimethylether, $CHClF_2$, $CH_2F_2$, $CF_3CH_3$, isobutane, isopentane and neopentane are used in addition to the propellent gases HFA 227 and/or HFA 134a in the suspension formulations according to the invention, the amount of this additional propellent gas component is preferably less than 50%, preferably less than 40%, particularly preferably less than 30%.

The suspensions according to the invention preferably contain an amount of tiotropium bromide anhydrate such that the amount of tiotropium cation is between 0.001 and 0.8%, preferably between 0.08 and 0.5%, and particularly preferably between 0.2 and 0.4% according to the invention.

Unless stated to the contrary, the percentages given within the scope of the present invention are always percent by weight.

In some cases, the term suspension formulation is used within the scope of the present invention instead of the term suspension. The two terms are to be regarded as equivalent within the scope of the present invention.

The propellant-containing inhalable aerosols or suspension formulations according to the invention may also contain other constituents such as surface-active agents (surfactants), adjuvants, antioxidants or flavourings.

The surface-active agents (surfactants) optionally present in the suspensions according to the invention are preferably selected from the group consisting of Polysorbate 20, Polysorbate 80, Myvacet 9-45, Myvacet 9-08, isopropyl myristate, oleic acid, propyleneglycol, polyethyleneglycol, Brij, ethyl oleate, glyceryl trioleate, glyceryl monolaurate, glyceryl monooleate, glyceryl monostearate, glyceryl monoricinoleate, cetylalcohol, sterylalcohol, cetylpyridinium chloride, block polymers, natural oil, ethanol and isopropanol. Of the above-mentioned suspension adjuvants Polysorbate 20, Polysorbate 80, Myvacet 9-45, Myvacet 9-08 or isopropyl myristate are preferably used. Myvacet 9-45 or isopropyl myristate are most preferably used.

If the suspensions according to the invention contain surfactants these are preferably used in an amount of 0.0005-1%, particularly preferably 0.005-0.5%.

The adjuvants optionally contained in the suspensions according to the invention are preferably selected from the group consisting of alanine, albumin, ascorbic acid, aspartame, betaine, cysteine, phosphoric acid, nitric acid, hydrochloric acid, sulphuric acid and citric acid. Ascorbic acid, phosphoric acid, hydrochloric acid or citric acid are preferably used, while hydrochloric acid or citric acid is most preferably used.

If adjuvants are present in the suspensions according to the invention, these are preferably used in an amount of 0.0001-1.0%, preferably 0.0005-0.1%, particularly preferably 0.001-0.01%, while an amount of 0.001-0.005% is particularly important according to the invention.

The antioxidants optionally contained in the suspensions according to the invention are preferably selected from the group consisting of ascorbic acid, citric acid, sodium edetate, editic acid, tocopherols, butylhydroxytoluene, butylhydroxyanisol and ascorbylpalmitate, while tocopherols, butylhydroxytoluene, butylhydroxyanisol or ascorbylpalmitate are preferably used.

The flavourings optionally contained in the suspensions according to the invention are preferably selected from the group consisting of peppermint, saccharine, Dentomint, aspartame and ethereal oils (for example cinnamon, aniseed, menthol, camphor), of which peppermint or Dentomint® are particularly preferred.

With a view to administration by inhalation it is essential to provide the active substances in finely divided form. For this purpose, the crystalline tiotropium bromide anhydrate according to the invention is obtained in finely divided form using methods known in the prior art. Methods of micronising active substances are known in the art. Preferably after micronising the active substance has a mean particle size of 0.5 to 10 μm, preferably 1 to 6 μm, particularly preferably 1.5 to 51 μm. Preferably at least 50%, preferably at least 60%, particularly preferably at least 70% of the particles of active substance have a particle size which is within the size ranges mentioned above. Particularly preferably at least 80%, most preferably at least 90% of the particles of active substance have a particle size which is within the size ranges mentioned above.

In another aspect the present invention relates to suspensions which contain only one of the two active substances according to the invention without any other additives.

The suspensions according to the invention may be prepared using methods known in the art. For this, the constituents of the formulation are mixed with the propellent gas or gases (optionally at low temperatures) and filled into suitable containers.

The above-mentioned propellant-containing suspensions according to the invention may be administered using inhalers known in the art (pMDIs=pressurized metered dose inhalers). Accordingly, in another aspect, the present invention relates to pharmaceutical compositions in the form of suspensions as hereinbefore described combined with one or more inhalers suitable for administering these suspensions. Moreover the present invention relates to inhalers, characterised in that they contain the propellant-containing suspensions according to the invention described hereinbefore.

The present invention also relates to containers (cartridges) which when fitted with a suitable valve can be used in a suitable inhaler and which contain one of the above-mentioned propellant-containing suspensions according to the invention. Suitable containers (cartridges) and processes for filling these cartridges with the propellant-containing suspensions according to the invention are known in the art.

In view of the pharmaceutical activity of tiotropium the present invention also relates to the use of the suspensions according to the invention for preparing a pharmaceutical composition for inhalation or nasal administration, preferably for preparing a pharmaceutical composition for inhalative or nasal treatment of diseases in which anticholinergics may develop a therapeutic benefit.

Particularly preferably the present invention also relates to the use of the suspensions according to the invention for preparing a pharmaceutical composition for the inhalative treatment of respiratory complaints, preferably asthma or COPD.

The Examples that follow serve to illustrate the present invention in more detail, by way of example, without restricting it to their contents.

B.2.1 Examples of Aerosol Suspension Formulations

Suspensions containing other ingredients in addition to active substance and propellent gas:

Formulation Example 8

| constituents | concentration [% w/w] |
| --- | --- |
| tiotropium bromide anhydrate | 0.04 |
| oleic acid | 0.005 |
| HFA-227 | 99.955 |

Formulation Example 9

| constituents | concentration [% w/w] |
| --- | --- |
| tiotropium bromide anhydrate | 0.02 |
| oleic acid | 0.01 |
| HFA-227 | 60.00 |
| HFA-134a | 39.97 |

Formulation Example 10

| constituents | concentration [% w/w] |
| --- | --- |
| tiotropium bromide anhydrate | 0.02 |
| isopropylmyristate | 1.00 |
| HFA-227 | 98.98 |

Formulation Example 11

| constituents | concentration [% w/w] |
| --- | --- |
| tiotropium bromide anhydrate | 0.02 |
| Myvacet 9-45 | 0.3 |
| HFA-227 | 99.68 |

Formulation Example 12

| constituents | concentration [% w/w] |
| --- | --- |
| tiotropium bromide anhydrate | 0.02 |
| Myvacet 9-45 | 0.1 |
| HFA-227 | 60.00 |
| HFA-134a | 39.88 |

Formulation Example 13

| constituents | concentration [% w/w] |
| --- | --- |
| tiotropium bromide anhydrate | 0.04 |
| Polysorbate 80 | 0.04 |
| HFA-227 | 99.92 |

Formulation Example 14

| constituents | concentration [% w/w] |
| --- | --- |
| tiotropium bromide anhydrate | 0.01 |
| Polysorbate 20 | 0.20 |
| HFA-227 | 99.78 |

Formulation Example 15

| constituents | concentration [% w/w] |
| --- | --- |
| tiotropium bromide anhydrate | 0.04 |
| Myvacet 9-08 | 01.00 |
| HFA-227 | 98.96 |

Formulation Example 16

| constituents | concentration [% w/w] |
| --- | --- |
| tiotropium bromide anhydrate | 0.02 |
| isopropylmyristate | 0.30 |
| HFA-227 | 20.00 |
| HFA-134a | 79.68 |

Suspensions containing only active substance and propellent gas:

Formulation Example 17

| constituents | concentration [% w/w] |
| --- | --- |
| tiotropium bromide anhydrate | 0.02 |
| HFA-227 | 60.00 |
| HFA-134a | 39.98 |

Formulation Example 18

| constituents | concentration [% w/w] |
| --- | --- |
| tiotropium bromide anhydrate | 0.02 |
| HFA-227 | 99.98 |

Formulation Example 19

| constituents | concentration [% w/w] |
| --- | --- |
| tiotropium bromide anhydrate | 0.02 |
| HFA-134a | 99.98 |

Formulation Example 20

| constituents | concentration [% w/w] |
| --- | --- |
| tiotropium bromide anhydrate | 0.02 |
| HFA-227 | 99.98 |

Formulation Example 21

| constituents | concentration [% w/w] |
| --- | --- |
| tiotropium bromide anhydrate | 0.02 |
| HFA-134a | 99.98 |

Formulation Example 22

| constituents | concentration [% w/w] |
| --- | --- |
| tiotropium bromide anhydrate | 0.02 |
| HFA-227 | 20.00 |
| HFA-134a | 79.98 |

Formulation Example 23

| constituents | concentration [% w/w] |
| --- | --- |
| tiotropium bromide anhydrate | 0.04 |
| HFA-227 | 40.00 |
| HFA-134a | 59.96 |

Formulation Example 24

| constituents | concentration [% w/w] |
| --- | --- |
| tiotropium bromide anhydrate | 0.04 |
| HFA-227 | 80.00 |
| HFA-134a | 19.96 |

The invention claimed is:

1. Anhydrous crystalline tiotropium bromide which is characterized in that the X-ray powder diagram has values d=6.02 Å; 4.95 Å; 4.78 Å; 3.93 Å and 3.83 Å.

2. A pharmaceutical composition comprising crystalline anhydrous tiotropium bromide according to claim 1 and a pharmaceutically acceptable carrier or excipient thereof.

3. The pharmaceutical composition according to claim 2, which is in the form of an inhalable powder.

4. The pharmaceutical composition according to claim 3, wherein the inhalable powder, in addition to the anhydrous crystalline tiotropium bromide, comprises one or more suitable physiologically acceptable excipients selected from monosaccharides, disaccharides, oligo- and polysaccharides, olyalcohols, cyclodextrins, and amino acids or salts or mixtures thereof.

5. The pharmaceutical composition according to claim 4, wherein the excipient is selected from the group consisting of glucose, fructose, arabinose, lactose, saccharose, maltose, trehalose, dextrans, dextrins, maltodextrin, starch, cellulose, sorbitol, mannitol, xylitol, α-cyclodextrin, β-cyclodextrin, χ-cyclodextrin, methyl-β-cyclodextrin, hydroxypropyl-β-cyclodextrin, arginine hydrochloride, sodium chloride and calcium carbonate or mixtures thereof.

6. The pharmaceutical composition according to claim 4 or 5, which comprises between 0.01 and 2% tiotropium.

7. The pharmaceutical composition according to claim 2, which is in the form of a capsule.

8. The pharmaceutical composition according to claim 2, which is in the form of a propellant-containing aerosol suspension formulation.

9. A method of treating respiratory complaints comprising administering to a patient in need thereof a crystalline anhydrous tiotropium bromide according to claim 1 and a pharmaceutically acceptable salt of excipient thereof.

10. The method of claim 9, wherein the respiratory complaint is selected from asthma or COPD.

* * * * *